United States Patent [19]

Kurono et al.

[11] Patent Number: 5,008,416

[45] Date of Patent: Apr. 16, 1991

[54] ORGANOGERMANIUM COMPOUND, PROCESS FOR THE PREPARATION OF SAME AS WELL AS USE THEREOF

[75] Inventors: Masayasu Kurono; Yasuaki Kondo; Takahiko Mitani; Yutaka Baba; Kiichi Sawai, all of Aichi, Japan

[73] Assignee: Sanwa Kagaku Kenkyusho Co., Ltd., Aichi, Japan

[21] Appl. No.: 540,535

[22] Filed: Jun. 19, 1990

[30] Foreign Application Priority Data

Jun. 20, 1989 [JP] Japan .................................. 1-155585
Nov. 20, 1989 [JP] Japan .................................. 1-299636

[51] Int. Cl.$^5$ .............................................. C07F 7/30
[52] U.S. Cl. ......................................... 556/89; 556/88; 556/83; 424/650
[58] Field of Search ........................... 556/88, 89, 83; 424/650

[56] References Cited

FOREIGN PATENT DOCUMENTS 0033292 2/1984 Japan ..................................... 556/89

Primary Examiner—Arthur C. Prescott
Assistant Examiner—Porfirio Nazario

Attorney, Agent, or Firm—Armstrong, Nikaido, Marmelstein, Kubovcik & Murray

[57] ABSTRACT

An organogermanium compound of the formula

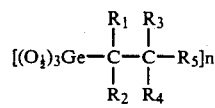

wherein $R_1$, $R_2$, $R_3$ and $R_4$ are hydrogen atom, alkyl, substituted alkyl, phenyl or substituted phenyl, and $R_5$ is a radical of

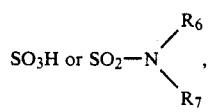

n is an integer of 2 or more, and $R_6$ and $R_7$ are hydrogen atom, alkyl, substituted alkyl, phenyl or substituted phenyl, a salt of the compound, a processs for the preparation of the compound as well as a use of the compound as an affective ingredient for pharmaceutical preparations.

2 Claims, 2 Drawing Sheets

ORGANOGERMANIUM COMPOUND, PROCESS FOR THE PREPARATION OF SAME AS WELL AS USE THEREOF

BACKGROUND OF THE INVENTION

1. Field of the Invention

The present invention relates to a novel organogermanium compound, a salt thereof, process for the preparation of the same as well as a use of the compound as an effective ingredient for pharmaceutical preparations.

2. Related Arts

Organogermanium compounds have been watched with great interests in recent years, since those show various and attractive pharmacological activities, so that various study reports have been issued, as stated below.

For instance, it has been reported that a compound (known in the art as "Y-9577") of the formula

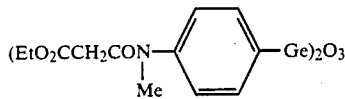

wherein Et is ethyl and Me is methyl, shows an antiinflammatory activity [Jap. Pat. Nos. Sho 56-45492(A), 56-99418(A), 56-99491(A) and 56-108708(A)]. It has also been reported that another compound (known in the art as "Spirogermanium") of the formula

wherein Et and Me have the meanings as referred to, shows an anti-cancer or antitumor activity ["Cancer Res.", Vol. 42, page 2852 (1982)].

Some of the present inventors have also studied on some organogermanium compounds and reported that 3-oxygermylpropionic acid polymer shows an excellent immunomodulating activity [Jap. Pat. No. Sho 61-151123(A) corresponding to U.S. Pat. No. 4,889,715 and EP No. 0186505 (A2)].

In spite of that various pharmacological activities have been reported on various organogermanium compounds, as referred to, the quantitative structure-activity relationships of organogermanium compounds and mechanism of pharmacological action have not yet been fully elucidated.

When the prior arts as referred to and experiences of the present inventors have been taken into consideration, it is so estimated on organogermanium compounds that a difference in structure exerts great influences on a kind of pharmacological activity and intensity thereof. Paradoxically speaking, this means that a preparation of novel organogermanium compound different from the conventional compounds in its structure and investigation of its pharmacological activities not only contribute to an elucidation of quantitative structure-activity relationships and mechanism of pharmacological action, but also give an expectancy of new pharmacological activity or an increase in activity, even though the kind of activity is same with that in the known organogermanium compounds.

OBJECTS AND SUMMARY OF THE INVENTION

A basic object of the invention is, therefore, to provide a novel organogermanium compound and salts thereof which show various and excellent pharmacological activities.

Another object of the invention is to provide a process for the preparation of such organogermanium compounds and salts thereof.

Still other object of the invention is to provide a pharmaceutical composition containing such a organogermanium compound or salt thereof.

According to the invention, the basic object can be attained by an organogermanium compound of the formula

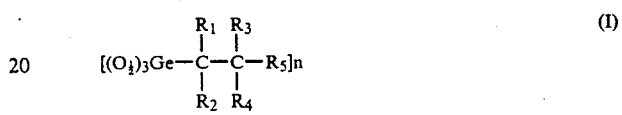

wherein $R_1$, $R_2$, $R_3$ and $R_4$ are hydrogen atom, alkyl, substituted alkyl, phenyl or substituted phenyl, and $R_5$ is a radical of

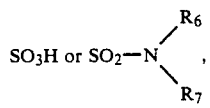

n is an integer of 2 or more, and $R_6$ and $R_7$ are hydrogen atom, alkyl, substituted alkyl, phenyl or substituted phenyl, and a salt thereof.

As the alkyl, methyl, ethyl, propyl, isopropyl, butyl, isobutyl, s-butyl, t-butyl, pentyl, hexyl or the like straight or branched-chain alkyl radicals having 1 to 6 carbon atoms can be listed. As the substituted alkyl, fluoromethyl, chloromethyl, difluoromethyl, trifluoromethyl, fluoroethyl, chloroethyl, bromoethyl, difluoroethyl, dichloroethyl, trifluoroethyl, trichloroethyl, fluoropropyl, chloropropyl, difluoropropyl, trifluoropropyl or the like halogenoalkyl; benzyl; or o-chlorobenzyl, m-chlorobenzyl, p-chlorobenzyl, p-nitrobenzyl, p-methoxybenzyl or the like substituted benzyl can be listed. As the substituted phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-difluorophenyl, 2,4-difluorophenyl, 2,5-difluorophenyl, 2,6-difluorophenyl, 3,4-difluorophenyl, 3,5-difluorophenyl, 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, 3,5-dihydroxyphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl or the like substituted phenyl radical having the substituents of 1 to 3 halogen atoms, hydroxy radicals, alkoxy radicals or the like on its phenyl ring can be listed.

As the salt of said organogermanium compound, that with sodium, potassium, calcium, magnesium, iron, zinc, copper, silver or the like metal; that with ammonia, that with methylamine, dimethylamine, ethanolamine, ethylenediamine, meglumine, dicyclohexylamine, benzylamine or the like organic base; that with lysine, arginine, ornithine, histidine, tryptophan, oxylysine, oxyarginine, homoarginine or the like basic amino acid can be listed.

According to a process of the invention, the compound of the formula

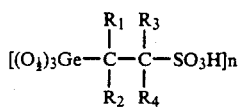 (I-a)

wherein $R_1$, $R_2$, $R_3$, $R_4$ and n have the meanings as referred to, and a salt thereof can be prepared by reacting a trihalogermanium compound of the formula

wherein X is a halogen atom, with an ethylene sulfide derivative of the formula

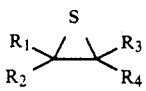

wherein $R_1$, $R_2$, $R_3$ and $R_4$ have the meanings as referred to, oxidizing resulting 2-trihalogermylethanethiol derivative of the formula

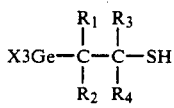

wherein $R_1$, $R_2$, $R_3$, $R_4$ and X have the meanings as referred to,
hydrolyzing resulting 2-trihalogermylethanesulfonic acid derivative of the formula

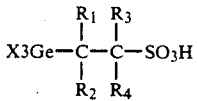

wherein $R_1$, $R_2$, $R_3$, $R_4$ and X have the meanings as referred to, and if necessary, converting the derivative into the salt.

In the process, the reaction between the trihalogermanium compound and the ethylene sulfide derivative can be carried out by stirring the reactants in the presence or absence of a solvent and at 0°-80° C., more preferably at room temperature. In this case, it unnecessary to isolate resulting 2-trihalogermylethanethiol from the reaction mixture which shall be employed for the subsequent oxidation step for converting into 2-trihalogermylethanesulfonic acid derivative. The oxidation reaction can easily be carried out with use of a conventional oxidant such as hydrogen peroxide, organoperoxoacid, peroxosurfuric acid, potassium permanganate, chromic acid, nitric acid, hydrogen bromide, hypochrorite, hypobromite, nitrogen peroxide, potassium hyperoxide, dimethylsulfoxide or the like. As the oxidant, it is preferable to use hydrogen peroxide. In this case, the reaction proceeds in any of neutral, acidic or basic condition, and it can be remarkably promoted by adding an acid catalyst of acetic acid, formic acid, methanesulfonic acid or the like, or a metal catalyst of tungsten, molybdenum, titanium, osmium, chromium or the like.

2-Trihalogermylethanesulfonic acid derivative can be isolated in a usual manner, but a treatment with an ion-exchange resin, which utilizes the presence of sulfonic acid residue in the product, makes the isolation more easy.

The final step of hydrolyzing 2-trihalogermylethanesulfonic acid derivative can easily be carried out with use of water, a basic aqueous solution or a mixture thereof with an organic solvent, and the desired 2-oxygermylethanesulfonic acid derivative can be isolated in a usual manner.

The step for converting the derivative into a salt can also be easily carried out, for instance, by mere mixing the derivative with a desired base. The salt can be obtained in the form of crystals or crystalline powder through freeze-drying or a treatment using a suitable solvent such as acetone, methanol, ethanol, dioxane or the like. If the hydrolyzing step is carried out in an aqueous solution containing a desired base, further, the salt of 2-oxygermylethanesulfonic acid derivative can directly be obtained.

The organogermanium compound of the formula

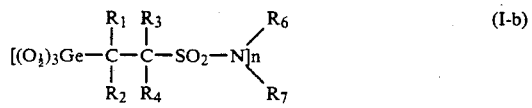 (I-b)

wherein $R_1$, $R_2$, $R_3$, $R_4$, $R_6$, $R_7$ and n have the meanings as referred to,
and a salt can be prepared by reacting 2-oxygermylethanesulfonic acid derivative of the formula

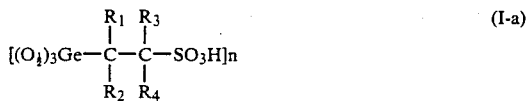 (I-a)

wherein $R_1$, $R_2$, $R_3$, $R_4$ and n have the meanings as referred to,
or a salt thereof with a halogenation reagent, reacting resulting 2-trihalogermylethanesulfonylhalide derivative of the formula

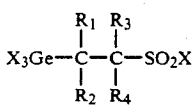

wherein $R_1$, $R_2$, $R_3$, $R_4$ and X have the meanings as referred to,
with an amine of the formula

wherein $R_6$ and $R_7$ have the meanings as referred to, hydrolyzing resulting compound, and if necessary converting the derivative into the salt.

In the process, the reaction between 2-oxygermylethanesulfonic acid or salt thereof and the halogenation reagent can easily be carried out in the presence or absence of a solvent and at room temperature to 150° C. As the halogenation reagent, phosphorus pentachloride, phosphorus oxychloride, thionyl chloride, chlorosurfuric acid, benzotrichloride or the like can be used. As the salt of 2-oxygermylethanesulfonic acid derivative, it is preferable to select that with sodium, potassium, ammonia, pyridine or the like.

After completion of the reaction, the resulting 2-trihalogermylethanesulfonic acid can be obtained through concentration of the reaction mixture and subsequent extraction with organic solvent. Otherwise, the reaction mixture is post-treated with water to convert the compound into 2-oxygermylethanesulfonyl halide derivative to isolate in the form of the latter.

While the reaction between 2-trihalogermylethanesulfonyl halide derivative and the amine can easily be carried out in the presence or absence of a solvent at 0°–80° C. An amount of amine to be used is at least 1 equivalent, but it is, in general, suitable to use 2–3 equivalents. As an acid receptor, potassium carbonate, sodium carbonate, triethylamine, quinoline, DBU or the like may be added in the reaction system. In this case, the amount of amine can be decreased.

2-Trihalogermylethanesulfonamide derivative can be isolated in a usual manner, and then the derivative is hydrolyzed in water, basic aqueous solution or a mixture thereof with an organic solvent to prepare the desired 2-oxygermylethanesulfonamide derivative. However, it is preferable to add the reaction mixture to water or the like to cause hydrolysis thereof into the desired 2-oxygermylethanesulfonamide derivative, since the isolation of 2-trihalogermylethanesulfonamide derivative can be omitted.

The organogermanium compound (I-b) can also be prepared by hydrolyzing 2-trihalogermylethanesulfonyl halide derivative of the formula

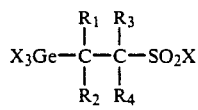

wherein $R_1$, $R_2$, $R_3$, $R_4$ and X have the meanings as referred to,
reacting resulting 2-oxygermylethanesulfonyl halide derivative of the formula

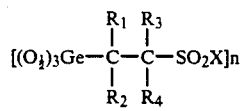

wherein $R_1$, $R_2$, $R_3$, $R_4$, X and n have the meanings as referred to,
with an amine of the formula $HNR_6R_7$ wherein $R_6$ and $R_7$ have the meanings as referred to, and if necessary, converting the derivative into the salt.

2-Trihalogermylethanesulfonyl halide derivative as the raw material for the process can be prepared by starting from 2-oxygermylethanesulfonic acid derivative to convert the same into 2-trihalogermylethanesulfonic acid derivative and then reacting with a halogenation reagent. 2-Trihalogermylethanesulfonic acid derivative can easily be obtained by reacting 2-oxygermylethanesulfonic acid derivative with hydrochloric acid, hydrogen bromide, hydrogen iodide or the like, for instance, if it reacted with concentrated hydrochloric acid, 2-trichlorogermylethanesulfonic acid derivative can be obtained. The hydrolysis of this 2-trihalogermylethanesulfonic acid derivative can be carried out in water, basic aqueous solution or a mixture thereof with an organic solvent, as in the aforesaid process. The reaction between 2-oxygermylethanesufonyl halide derivative as hydrolyzed product and the amine is same with that in the aforesaid process.

The organogermanium compound (I-b) can also be prepared by converting 2-oxygermylethanesulfonic acid derivative of the formula

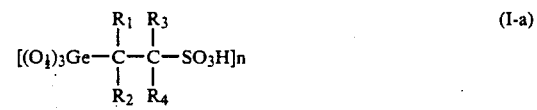

wherein $R_1$, $R_2$, $R_3$, $R_4$ and n have the meanings as referred to,
or a salt thereof into an anhydrous 2-trihalogermylethanesulfonic anhydride derivative of the formula

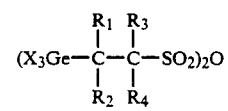

wherein $R_1$, $R_2$, $R_3$, $R_4$ and X have the meanings as referred to,
reacting the anhydride derivative with an amine of the formula $HNR_6R_7$ wherein $R_6$ and $R_7$ have the meanings as referred to, hydrolyzing resulting reaction product, and if necessary, converting the derivative into the salt.

The conversion into anhydride, as the first step of the above process can be carried out with use of thionyl chloride, phosphorus pentaoxide, N,N'-dicyclohexylcarbodiimide (DCC) or the like. The second step of the reaction with the amine as well as the third step of hydrolysis are same with the aforesaid process.

The organogermanium compounds according to the invention show various biological activities, namely immunomodulating activity, enhancement of interferon production, anticancer or antitumor activity, anti-viral activity, hepatoprotective activity and others. Therefore, the compounds may be expected as an effective ingredient for various pharmaceutical preparations to cure immunity acceleration and inhibition diseases, virosis, cancerous or tumorous diseases, liver injury and the like.

Turning now to that in recent years, the spreading of acquired immune deficiency syndrome (AIDS) becomes a serious public problem and the virus causing the disease has been estimated as Human Immunodeficiency Virus (HIV). For curing the disease, at the present time, inhibitors of nucleic acid synthesis have been mainly administered. This type drug shows virus killing activity but also shows a strong side effect to destroy normal tissue, so that a development of more safety drug has urgently been required.

Since the organogermanium compounds according to the invention show not only the immunomodulating activity inclusive of immunoactivating effect but also the enhancement of interferon production (interferon has been established as one of anti-HIV substance), so that the organogermanium compounds have higher possibility of utilizing as a new type drug for curing AIDS.

DETAILED DESCRIPTION OF PREFERRED EMBODIMENTS

Figure 1:
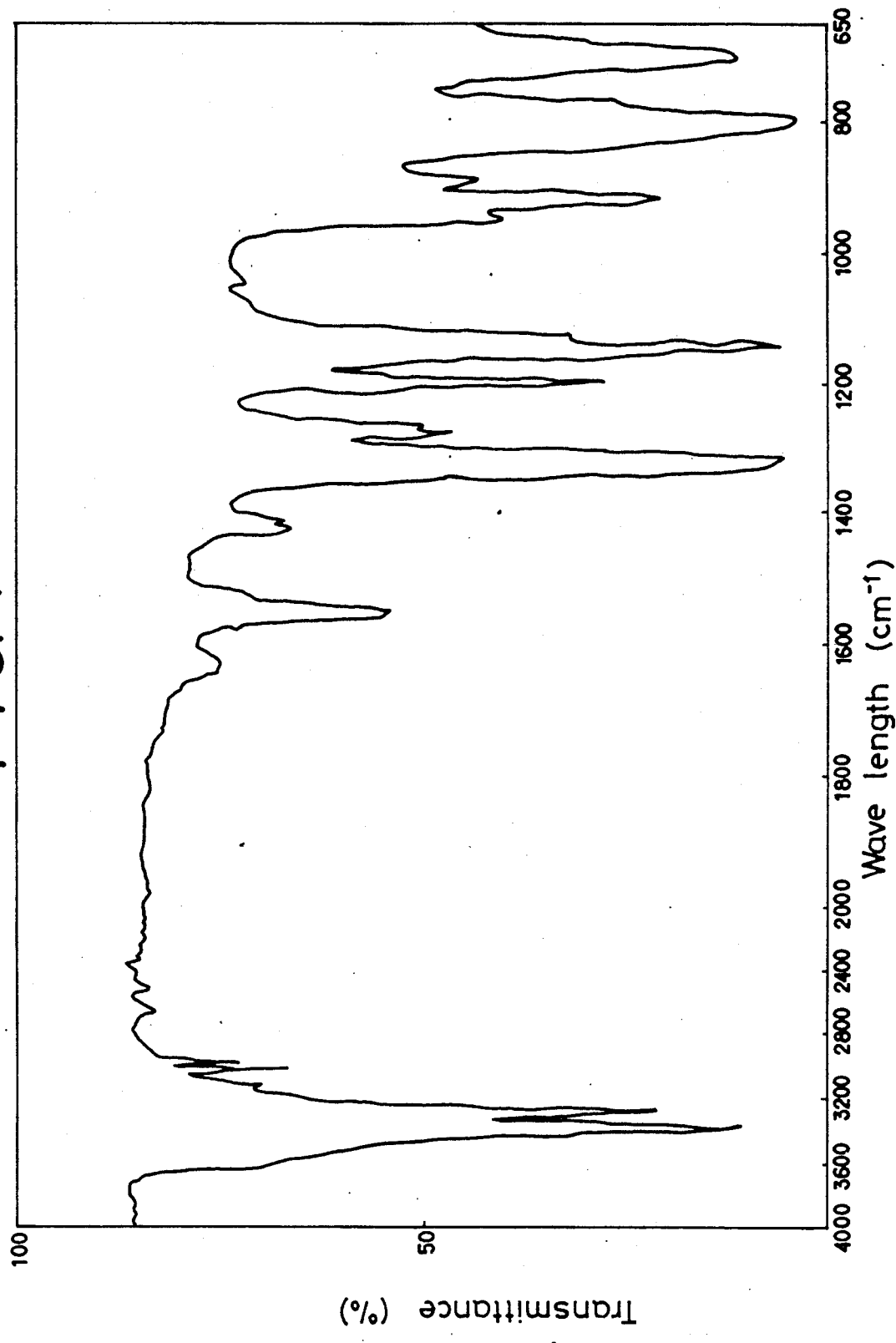
FIG. 1 is a graph showing IR spectrum measured on an organogermanium compound obtained by Example 10.

The invention will now be further explained in more detail with reference to Examples and Pharmacological Experiments.

EXAMPLE 1

2-Oxygermylethanesulfonic acid polymer

A solution of germanium hydroxide (6.40 g) in 1.80M HCl-ether solution (100 ml) was stirred at room temperature. To the solution under ice-cooling, ethylene sulfide (5.41 g) was added dropwise to further stir for 70 hours at room temperature.

After removed insoluble materials by filtration, the filtrate was concentrated in vacuo to add water (6.0 ml) and methanesulfonic acid (576 mg). To the mixture heated to 100° C., 31% aqueous hydrogen peroxide solution (59 ml) was added over 2 hours under stirring, heated for further 30 minutes, and left to stand for cooling.

The cooled reaction mixture was chromatographed over Diaion WA-21 eluting with 0.5N aqueous ammonia solution, concentrated in vacuo, and suspended in methanol to obtain crystals by filtration. The crystals were dissolved in water, treated with Diaion PK-216, concentrated resulting eluate in vacuo to afford the desired polymer as colorless glass-like substance (Yield: 7.41 g).

$^1$H-NMR spectrum (D$_2$O) δ ppm: 1.6–2.0 (2H, m, —GeCH$_2$CH$_2$S—), 2.9–3.3 (2H, m, —GeCH$_2$CH$_2$S—).

IR spectrum ($\nu_{max}^{KBr}$) cm$^{-1}$: 1150, 1030 (SO$_2$), 820 (Ge—O—).

EXAMPLE 2

Ammonium 2-oxygermylethanesulfonate polymer

A solution of germanium hydroxide (3.20 g) in 1.80M HCl-ether solution (50 ml) was stirred at room temperature. To the solution under ice-cooling, ethylene sulfide (2.71 g) was added dropwise to stir for 70 hours at room temperature.

After removed insoluble materials by filtration, the filtrate was concentrated in vacuo to add water (3.0 ml) and methanesulfonic acid (288 mg). To the mixture heated to 100° C., 31% aqueous hydrogen peroxide solution (25 ml) was added over 2 hours under stirring, heated for further 30 minutes, and left to stand for cooling.

The cooled reaction mixture was chromatographed over Diaion WA-21 eluting with 0.5N aqueous ammonia solution, concentrated in vacuo, and suspended in methanol to obtain crystals by filtration. The crystals were recrystallized from water-methanol to afford the desired polymer (Yield: 3.50 g).

Melting point: >300° C.

$^1$H-NMR spectrum (D$_2$O) δ ppm: 1.6–2.0 (2H, m, —GeCH$_2$CH$_2$S—), 2.9–3.3 (2H, m, —GeCH$_2$CH$_2$S—).

IR spectrum ($\nu_{max}^{KBr}$) cm$^{-1}$: 3400–2800 (NH$_4$+), 1400 (NH$_4$+), 1185, 1040 (SO$_2$), 790 (Ge—O—).

EXAMPLE 3

2-Trichlorogermylethanesulfonic acid

To a solution of ammonium 2-oxygermylethanesulfonate polymer (2.23 g, obtained by Example 2) in 1.80M HCl-ether solution (25 ml), acetone (50 ml) was added to remove forming crystals by filtration, concentrating in vacuo the filtrate to afford the desired compound as colorless oil (Yield: 2.85 g).

$^1$H-NMR spectrum (acetone-d$_6$) δ ppm: 2.2–2.6 (2H, m, —GeCH$_2$CH$_2$S—), 3.0–3.4 (2H, m, —GeCH$_2$CH$_2$S—).

EXAMPLE 4

Sodium 2-oxygermylethanesulfonate polymer

To a solution of 2-oxygermylethanesulfonic acid polymer (2.06 g, obtained by Example 1) in water (30 ml), 1.00N NaOH solution (10 ml) was added and freeze-dried to afford the desired polymer (2.28 g).

Melting point: >300° C.

$^1$H-NMR spectrum (D$_2$O) δ ppm: 1.6–2.0 (2H, m, —GeCH$_2$CH$_2$S—), 2.9–3.3 (2H, m, —GeCH$_2$CH$_2$S—).

IR spectrum ($\nu_{max}^{KBr}$) cm$^{-1}$: 1190, 1045 (SO$_2$), 790 (Ge—O—).

EXAMPLE 5

Sodium 2-oxygermylethanesulfonate polymer

To a solution of 2-oxygermylethanesulfonic acid polymer (1.03 g, obtained by Example 1) in water (10 ml), 1.00N NaOH solution (5.0 ml) was added, concentrated in vacuo, and recrystallized from water-methanol to afford the desired polymer (1.08 g).

Physico-chemical data of this polymer coincide with those given in Example 4.

EXAMPLE 6

Ammonium 2-oxygermylethanesulfonate polymer

To a solution of 2-oxygermylethanesulfonic acid polymer (1.03 g, obtained by Example 1) in water (20 ml), 1.00N aqueous ammonia solution (5.0 ml) was added and freeze-dried to afford the desired polymer (1.11 g).

Physico-chemical data of this polymer coincide with those given in Example 2.

EXAMPLE 7

2-Trichlorogermylethanesulfonyl chloride

A mixture of sodium 2-oxygermylethanesulfonate polymer (1.00 g, obtained by Example 1) and phosphorus pentachloride (4.57 g) was stirred for 6 hours at 100°–110° C.

The reaction mixture was concentrated in vacuo, dissolved in chloroform, removed insoluble materials, concentrated in vacuo the filtrate to afford the desired compound (Yield 1.20 g).

$^1$H-NMR spectrum (CDCl$_3$) δ ppm: 2.45–2.75 (2H, m, —GeCH$_2$CH$_2$S—), 3.75–4.05 (2H, m, —GeCH$_2$CH$_2$S—).

IR spectrum ($\nu_{max}^{neat}$) cm$^{-1}$: 1370, 1180, 1160 (SO$_2$), 890, 870, 760 (Ge—O—).

EXAMPLE 8

2-Oxygermylethanesulfonyl chloride polymer

A mixture of sodium 2-oxygermylethanesulfonate polymer (0.690 g, obtained by Example 4) and phosphorus pentachloride (3.30 g) was stirred for 6 hours at 100°–110° C.

To the reaction mixture, ice water (15 ml) was added to obtain forming crystals which were washed with water and dried to afford the desired polymer (Yield: 0.55 g).

IR spectrum ($\nu_{max}^{KBr}$) cm$^{-1}$: 1360, 1180, 1160 ($SO_2$), 905, 805 (Ge—O—).

EXAMPLE 9

2-Trichlorogermylethanesulfonic anhydride

A mixture of sodium 2-oxygermylethanesulfonic acid polymer (3.70 g, obtained by Example 1) and thionyl chloride (42.8 g) was refluxed for 6 hours under stirring, and then concentrated in vacuo to afford the desired compound (Yield: 4.51 g).

$^1$H-NMR spectrum (CDCl$_3$) δ ppm: 2.35–2.65 (2H, m, —GeC$\underline{H}_2$CH$_2$S—), 3.7–4.0 (2H, m, —GeCH$_2$C$\underline{H}_2$S—).

EXAMPLE 10

2-Oxygermylethanesulfonamide polymer

To chloroform solution (16.0 ml) saturated with ammonia, 2-trichlorogermylethanesulfonyl chloride (500 mg, obtained by Example 7) in chloroform solution (2.0 ml) was added dropwise and stirred for 22 hours at room temperature.

After added water (2.0 ml), the reaction mixture was concentrated in vacuo, and crystallized from methanol to afford the desired polymer (Yield: 260 mg).

Melting point: >300° C.

$^1$H-NMR spectrum (D$_2$O) δ ppm: 1.8–1.9 (2H, m, —GeC$\underline{H}_2$CH$_2$S—), 3.4–3.5 (2H, m, —GeCH$_2$C$\underline{H}_2$S—).

IR spectrum ($\nu_{max}^{KBr}$) cm$^{-1}$: 1315, 1140 ($\overline{SO_2}$), 910, 800 (Ge—O—).

IR spectrum of this polymer is also shown in FIG. 1.

EXAMPLE 11

2-Oxygermylethanesulfonamide polymer

2-Oxygermylethanesulfonyl chloride polymer (224 mg, obtained by Example 8) was added in concentrated aqueous ammonia solution (3.80 ml and stirred for 24 hours at room temperature.

The reaction mixture was concentrated in vacuo, crystallized from methanol, and recrystallized from water to afford the desired polymer (Yield: 145 mg).

Physico-chemical data of this polymer coincide with those given in Example 10.

EXAMPLE 12

2-Oxygermylethanesulfonamide polymer

To chloroform solution (10.0 ml) saturated with ammonia, 2-trichlorogermylethanesulfonic anhydride (307 mg, obtained by Example 9) in chloroform solution (1.0 ml) was added dropwise and stirred for 3.5 hours at room temperature.

After added water (0.5 ml), the reaction mixture was concentrated in vacuo, and crystallized from methanol to obtain 213 mg of white crystals.

The crystals were dissolved in water, chromatographed over Diaion WA-21 eluting with water, concentrated in vacuo, and crystallized from methanol to afford the desired polymer (Yield: 82 mg).

Physico-chemical data of this polymer coincide with those given in Example 10.

EXAMPLE 13

2-Oxygermylethanesulfonamide polymer

2-Oxygermylethanesulfonamide polymer (770 g, obtained by a method similar to that given in Example 10) was dissolved in water (160 ml) and then freeze-dried to obtain the titled compound which had following physico-chemical data.

Melting point: >300° C.

$^1$H-NMR spectrum (D$_2$O) δ ppm: 1.8–1.9 (2H, m, —GeC$\underline{H}_2$CH$_2$S—), 3.4–3.5 (2H, m, —GeCH$_2$C$\underline{H}_2$S—).

IR spectrum ($\nu_{max}^{KBr}$) cm$^{-1}$: 1325, 1145 ($\overline{SO_2}$), 880, 805 (Ge—O—).

Figure 2:
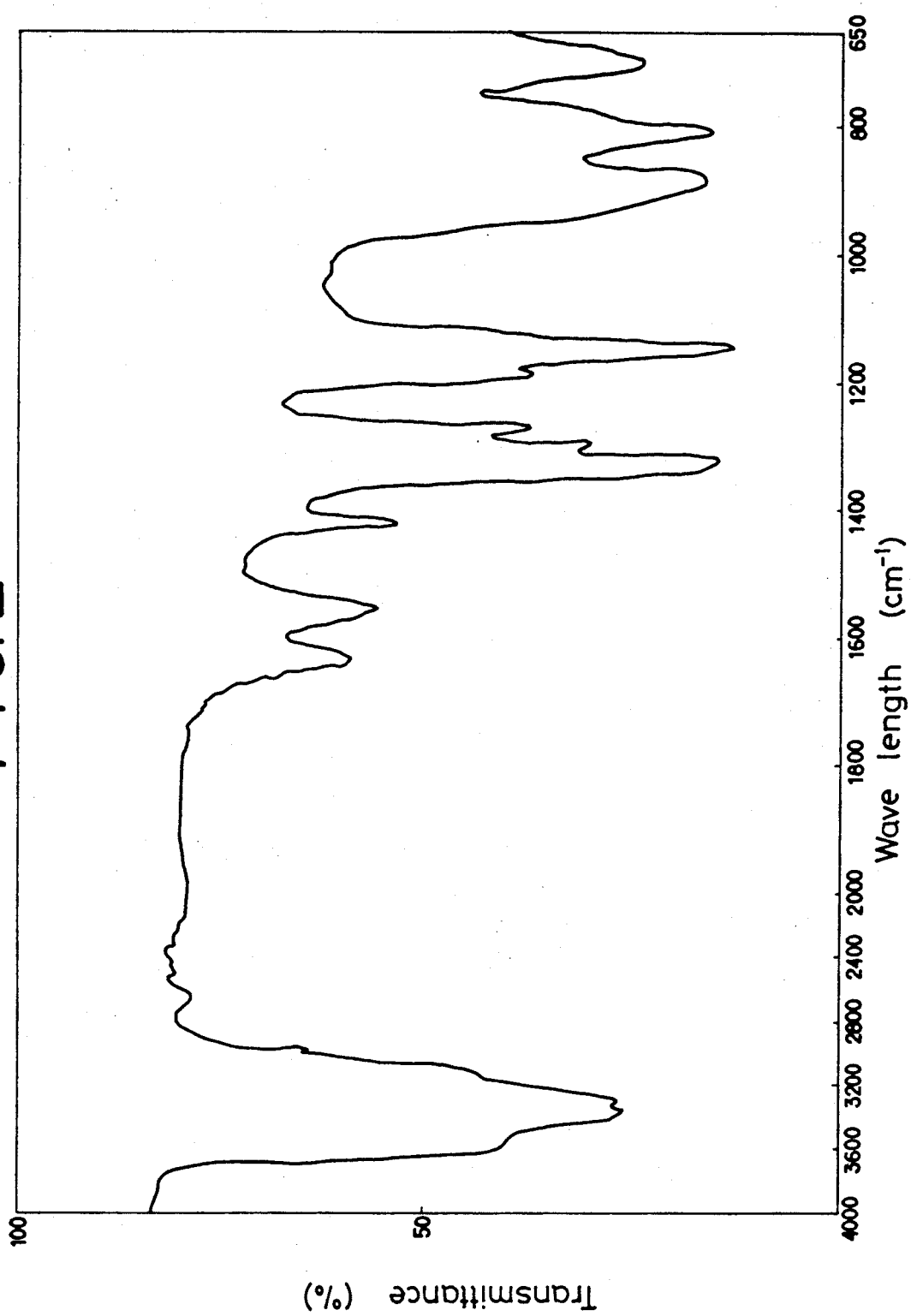
FIG. 2 is a graph showing IR spectrum measured on an organogermanium compound obtained by Example 13.

IR spectrum of this polymer is also shown in FIG. 2.

EXAMPLE 14

2-Trichlorogermylethanesulfonamide

To chloroform solution (16.0 ml) saturated with ammonia, 2-trichlorogermylethanesulfonylchloride (500 mg, obtained by Example 7) in chloroform solution (2.0 ml) was added dropwise and stirred for 22 hours at room temperature.

The reaction mixture was concentrated in vacuo, adding therein concentrated hydrochloric acid, extracted with chloroform, and then further concentrated in vacuo to afford the desired compound (Yield: 365 mg).

$^1$H-NMR spectrum (CDCl$_3$) δ ppm: 2.3–2.7 (2H, m, —GeC$\underline{H}_2$CH$_2$S—), 3.2–3.6 (2H, m, —GeCH$_2$C$\underline{H}_2$S—), 4.6–5.1 (2H, br, —NH$_2$).

The invention will now be further explained with reference to Pharmacological Experiments. In the Experiments, sodium 2-oxygermylethanesulfonate polymer (obtained by Example 4) was selected as—Test Compound—, but please note that other organogermanium compounds according to the invention show pharmacological activities similar to the Test Compound.

Pharmacological Experiment 1

(Influence on antibody production)

(a) Object

Influence of the organogermanium compound on antibody production ability is checked with use of tumor bearing mice, as experimental animals reduced in their immunity response.

(b) Methods

Tumor bearing mice were prepared by implanting $2 \times 10^6$ cells of mouse tumor cell (Sarcoma 180) under a skin of each ICR male mouse (age of 6 weeks) to form a solid tumor.

The organogermanium compound (Production Example 4) dissolved in 4% bovine serum albumin solution was orally administered to the tumor bearing mice over 5 days after lapsed 9 days from the implantation of the tumor cells, by a dose of 0.1, 1.0 or 10.0 mg/kg/day.

After lapsed 14 days from the implantation, $2 \times 10^8$ cells of sheep red blood cells (SRBC) were injected in a tail vein of the mice for sensitization. After 4 days from the sensitization, spleen was removed and number of PFC in $10^6$ spleen cells was measured, as an index of the antibody production in the tumor bearing mice.

(c) Results and discussion

Results are shown in following Table 1. It can be seen that the reduced antibody production due to generation of the tumor increased to a normal level, depending on an administration and more particularly an dosing amount of the organogermanium compound.

TABLE 1

| Group | Dose (m/k) | Number of PFC (#) |
|---|---|---|
| Normal | — | 1061 ± 217 (*) |
| Tumor bearing | — | 508 ± 79 |
| Drug dosed | 0.1 | 745 ± 66 (*) |
| Drug dosed | 1.0 | 948 ± 195 |
| Drug dosed | 10.0 | 1071 ± 89 (***) |

In the Table,
# : mean ± standard error value, (n = 7);
* : significant difference from tumor bearing mice group giving no compound ($p < 0.05$);
*** : significant difference from tumor bearing mice group giving no compound ($p < 0.001$).

Pharmacological Experiment 2

(Influence on antibody production)

(a) Object

Influence of the organogermanium compound on antibody production is checked with use of NZB/WF$_1$ mice who generate an autoimmune disease due to polyclonal activation of B cells, caused by functional reduction of suppresser T cell activities.

(b) Methods

NZB/WF$_1$ female mice (age of 11 weeks) were classified into Control group and Test groups (5 mice for each group), and $2 \times 10^8$ cells of SRBC were injected in a tail vein of each mouse for sensitization.

To the mice in each Test group, the organogermanium compound (Example 4) dissolved in 4% bovine serum albumin solution was orally administered in a dose of 1.0 or 10.0 mg/kg/day at 3 time, namely the day before, just after and the day after the sensitization.

After 4 days from the sensitization, spleen was removed from each mouse and number of PFC in 10$^6$ spleen cells was measured, as an index of the antibody production in the NZB/WF$_1$ mice.

(c) Results and discussion

Results are shown in following Table 2. It can be seen therefrom that the number of PFC increases in the Control group, but in the treatment groups, the number of PFC was significantly reduced.

By taking the results shown in Table 2 and results obtained by Pharmacological Experiment 1, namely the recovery of antibody production ability reduced by tumor bearing into consideration, it can be said that the organogermanium compound according to the invention has an immunomodulating activity.

TABLE 2

| Group | Dose (m/kg) | Number of PFC (#) |
|---|---|---|
| Control | — | 5110 ± 240 |
| Test A | 1.0 | 3511 ± 302 (*) |
| Test B | 10.0 | 3800 ± 360 (*) |

In the Table,
# : mean ± standard error value, (n = 5);
* : significant difference from Control group giving no compound ($p < 0.05$);
* : significant difference from Control group giving no compound ($p < 0.01$).

Pharmacological Experiment 3

(Influence on delayed type hypersensitivity)

(a) Object

To investigate the effect of the organogermanium compound on the cellular immunity, we employed the delayed type hypersensitivity (DTH) of mice. Tumor bearing mice were used as experimental animals with reduced immunity and effect of the compound on the reduced DTH reaction was assayed.

(b) Methods

Sarcoma 180 cells ($10^6$ cells) were intraperitoneally implanted to ICR male mice (age of 8 weeks) and after 3 hours from the implantation, $10^6$ cells of SRBC were injected by intravenous route. Four days later, $2 \times 10^8$ cells of SRBC were intracutaneus injection to hind foot pad. After 24 hours from the injection, the swelling of the foot pad was observed by stereoscopic microscope.

To the mice in each test group, the organogermanium compound (Example 4) dissolved in 4% bovine serum albumin was orally administered at the time 4 days before the immunization at the dose of 0.1, 1.0 and 10.0 mg/kg.

(c) Results and discussion

As shown in Table 3, organogermanium compound according to the invention significantly restored the reduced DTH response to normal level. The results indicated the enhancing effect of cellular immunity by the compound.

TABLE 3

| Group | Dose (mg/kg) | Foot pad swelling (#) |
|---|---|---|
| Normal | — | 117 ± 11.1 (***) |
| Tumor bearing | — | 48.9 ± 3.2 |
| Tumor bearing | 0.1 | 66.8 ± 7.5 |
| Tumor bearing | 1.0 | 85.0 ± 5.9 (***) |
| Tumor bearing | 10.0 | 74.3 ± 4.9 (***) |

In the Table,
# : mean ± standard error value, ($\times 0.01$ mm, n = 10);
*** : significant difference from tumor bearing mice group giving no compound ($p < 0.001$).

Pharmacological Experiment 4

(Influence on delayed type hypersensitivity)

(a) Object

Influence of the organogermanium compound on the DTH response of normal mice is investigated.

(b) Methods

Normal ICR male mice (age of 8 weeks) were immunized with $10^6$ cells of SRBC by intravenous route. On 4 days after immunization, the organogermanium compound (Example 4) dissolved in 4% bovine serum albumin was orally administered at the dose of 0.1, 1.0 and 10.0 mg/kg. Just after the treatment with the compound, mice were challenged to intracutaneus injection of $2 \times 10^8$ cells of SRBC to hind food pad.

After 24 hours from the injection, the swelling of the foot pad was observed by a stereoscopic microscope.

(c) Results and discussion

Results are shown in following Table 4. The organogermanium compound significantly reduced the DTH response of normal mice.

By taking the results in normal mice shown in Table 4 and results in tumor bearing mice that restored the depressed DTH response (Pharmacological Experiment 3) into consideration, it is apparent that the compound posses an immunomodulating activity. And, if taking the results that the compound modulates antibody production (Pharmacological Experiments 1 and 2) into consideration, it indicates that the compound not only modulates the humaral immunity but also modulates the cellular immunity.

TABLE 4

| Group | Dose (mg/kg) | Food pad swelling (#) |
|---|---|---|
| Control | — | 122.2 ± 11.0 |
| Treated A | 0.1 | 70.9 ± 9.1 (**) |
| B | 1.0 | 59.0 ± 6.6 (***) |
| C | 10.0 | 86.9 ± 10.2 (*) |

In the Table,
# : mean ± standard error value, (× 0.01 mm, n = 10);
significant difference from Control
* : $p < 0.05$,
** : $p < 0.01$, and
*** : $p < 0.001$.

Pharmacological Experiment 5

(Influence on interferon production)
(a) Object

Influence of the organogermanium compound on interferon (IFN) production ability is investigated.

(b) Method

BALB/c male mice were subjected to the experiment (n=5 for each group).

Influenza virus (A/PR/8 strain) was intratrachealy inoculated at 9.0 PFU/mouse. Immediately after the inoculation, the organogermanium compound (Example 4) dissolved in 4% bovine serum albumin solution was orally given to the mice at the dose of 0.1, 1.0 and 10.0 mg/kg. Three days later, lung was isolated and homogenized in 5 volumes of PBS. The homogenate was centrifuged at 20,000× g for 30 minutes to obtain a supernatant. IFN activity of this supernatant was assayed by the inhibition of vesicular stomatitis virus (VSV) induced cytopathic effect on L929 cell.

(c) Results and discussion

Results are shown in following Table 5. The IFN activities of the compound treatment group was significantly increased to about 2.5 and 2.8 times higher than the control group, at the dose of 1.0 and 10.0 mg/kg respectively. These dada show that the organogermanium compound accelerates the production IFN.

TABLE 5

| Group | Dose (mg/kg) | INF titer (#) |
|---|---|---|
| Control | — | 55.2 ± 8.9 |
| Treated A | 0.1 | 49.3 ± 5.3 |
| B | 1.0 | 138.3 ± 17.1 (**) |
| C | 10.0 | 156.7 ± 28.3 (**) |

In the Table,
# : mean ± standard error value, (IU/mg protein, n = 5);
** : significant difference from control group giving no compound ($p < 0.01$).

Pharmacological Experiment 6

(Anti-tumor effect)
(a) Object

An anti-tumor effect of the organogermanium compound according to the invention is examined.

(b) Methods

C57BL/6 male mice (n=10) as experimental animals were subcutaneously implanted with $1 \times 10^5$ cells of Lewis lung carcinoma to form a solid tumor. The organogermanium compound (Example 4) dissolved in 4% bovine serum albumin was orally administered at the dose of 0.1, 1.0 and 10.0 mg/kg once a day for 5 days on days 1 to 5 after the tumor implantation.

On 14th day from the implantation, formed solid tumor was removed and weighed. An antitumor effect represented the inhibitory percent of the compound on the development of solid tumor.

(c) Results and discussion

Results are shown in following Table 6. It is apparent therefrom that the compound significantly inhibited the growth of Lewis lung carcinoma.

TABLE 6

| Group | Dose (mg/kg) | Tumor weight (#),(g) | Inhibition (%) |
|---|---|---|---|
| Control | — | 1.90 ± 0.30 | |
| Treated | 0.1 | 1.77 ± 0.47 | 6.8 |
| Treated | 1.0 | 1.02 ± 0.16 (*) | 46.3 |
| Treated | 10.0 | 1.36 ± 0.31 | 28.4 |

In the Table,
# : mean value ± standard deviation value, (n = 10);
* : significant difference from Control group giving no compound ($p < 0.05$).

Pharmacological Experiment 7

(Anti-tumor effect)
(a) Object

An anti-tumor effect of the organogermanium compound according to the invention is examined to Sarcoma 180 tumor cells.

(b) Methods

Sarcoma 180 tumor cells were subcutaneously implanted with $2 \times 10^6$ cells to male ICR mice (n=10) as experimental animals to form a solid tumor. The organogermanium compound (Example 4) dissolved in 4% bovine serum albumin was orally administered at the dose of 0.1, 1.0 and 10.0 mg/kg once a day for 10 days on the day after the implantation.

On the 20th day from the implantation, formed solid tumor was removed and weighed. An antitumor effect represented the inhibitory percent of the compound on the development of solid tumor.

(c) Results and discussion

Results are shown in following Table 7. As apparent therefrom, the compound reduced the growth of Sarcoma 180 solid tumor cells.

TABLE 7

| Group | Dose (mg/kg) | Tumor weight (#),(g) | Inhibition (%) |
|---|---|---|---|
| Control | — | 2.61 ± 0.67 | |
| Treated | 0.1 | 1.87 ± 0.46 | 28 |
| Treated | 1.0 | 0.82 ± 0.22 (*) | 69 |
| Treated | 10.0 | 1.61 ± 0.29 | 38 |

In the Table,
# : mean ± standard error value (n = 10);
* : significant difference from Control group giving no compound ($p < 0.05$).

Pharmacological Experiment 8

(Anti-virus effect)
(a) Object

An antiviral effect of the compound according to the invention is investigated using to Vaccinia virus infected mice.

(b) Methods

Vaccinia virus (DI strain) was inoculated into the tail vein of male ddy m at $5 \times 10^5$ PFU/mouse. Immediately after the infection, the organogermanium compound (Example 4) dissolved in 4% bovine serum albumin solution was orally administered to the mice at the dose of 1.0 and 10.0 mg/kg.

On the 7th day from the virus infection, number of pocks generated on the tail was counted and an inhibitory percent was calculated from the results in control group and the compound treatment group.

(c) Results and discussion

Results are shown in following Table 8. As apparently seen therefrom, the compound has host defense function against Vaccinia virus infected mice.

TABLE 8

| Group | Dose (mg/kg) | Number of pocks (#) | Inhibition (%) |
|---|---|---|---|
| Control | — | 33 ± 3 | |
| Treated | 0.1 | 23 ± 2 (***) | 41.0 |
| Treated | 10.0 | 22 ± 4 (***) | 43.5 |

In the Table,
# : mean ± standard error value, (n = 10);
*** : significant difference from Control group giving no compound ($p < 0.001$).

Pharmacological Experiment 9

(Anti-virus effect)
(a) Object

An antiviral effect of the compound according to the invention is investigated with an experimental influenza virus infection model of mouse.

(b) Methods

Influenza virus (A/PR/S strain) was inoculated into a trachea of BALB/c male mice at 9.0 PFU/mouse. The organogermanium compound (Example 4) dissolved in 4% bovine serum albumin solution was orally administered at the dose of 0.1, 1.0 and 10.0 mg/kg once a day for 6 days from the day just after the infection to the 5th day therefrom.

A mortality of the mice was observed over 20 days from the virus infection.

(c) Results and discussion

Results are shown in following Table 9. In the Control group, some mice were died on the 8th day from the infection and all of them have been died until the 10th day from the infection. On the contrary thereto, in the Test groups and more particularly, the Test group by the dose of 1.0 mg/kg, the first death was observed on the 10th day from the infection and 4 mice alive at the time, when the test period of time (20 days from the infection) was lapsed.

On average life period of time, a significant difference has been recognized in each of Testing groups, in comparison with the average life in the Control group.

TABLE 9

| Group | Dose (mg/kg) | Average life (day) | Ratio of survival |
|---|---|---|---|
| Control | — | 9.1 | 0/10 |
| Test A | 0.1 | 10.0 (*) | 0/10 |
| Test B | 1.0 | 15.2 (***) | 4/10 |
| Test C | 10.0 | 13.7 (**) | 3/10 |

In the Table,
* : significant difference from Control group giving no compound ($p < 0.05$);
** : significant difference from Control group giving no compound ($p < 0.01$); and
*** : significant difference from Control group giving no compound ($p < 0.001$).

Pharmacological Experiment 10

(Action to acute liver injury)
(a) Object

An action of the organogermanium compound of the invention to an acute liver injury to be induced by galactosamine, as an experimental model for liver injury is checked, through measurement of serum transaminases, as indexes.

(b) Methods

To Wister male rats (n=10 for each group), galactosamine was administered into abdominal canal by a dose of 400 mg/kg at 2 times with an interval of 6 hours to induce a acute liver injury.

To the mice in each Test group, the compound according to the invention (Example 4) dissolved in 4% bovine serum albumin solution was orally administered by 0.1, 1.0 or 10.0 mg/kg/day over 5 days beginning from 3 days before the administration of galactosamine.

After having lapsed 48 hours from the first administration of galactosamine, a blood letting was carried out to measure GOT and GPT values in serum.

(c) Results and consideration

Results are shown in following Table 10. As apparently seen therefrom that the compound according to the invention has an action for noticeably decreasing GOT and GPT values which were raised up by the administration of galactosamine.

TABLE 10

| Group | Dose (mg/kg) | s-GOT | s-GPT (#) (Karmen Unit) |
|---|---|---|---|
| No-treatment | — | 120 ± 7 (*) | 42 ± 5 (*) |
| Control | — | 1840 ± 267 | 717 ± 167 |
| Test A | 0.1 | 1034 ± 184 (*) | 382 ± 151 |
| Test B | 1.0 | 563 ± 133 (***) | 238 ± 87 (*) |
| Test C | 10.0 | 620 ± 201 (**) | 275 ± (*) |

In the Table,
# : mean ± standard error value, (n = 10);
Significant difference from Control:
* : $p < 0.05$,
** : $p < 0.01$, and
*** : $p < 0.001$.

Pharmacological Experiment 11

(Action to chronic liver injury)
(a) Object

An action of the organogermanium compound of the invention to a chronic liver injury to be induced by carbon tetrachloride, as an experimental model for liver injury is checked, through measurement of serum transaminases, as indexes.

(b) Methods

To Wister male rats (n=10 for each group), carbon tetrachloride was intraperitoneally administered at the dose of 480 mg/kg at 2 times by each week for 10 weeks to induce a chronic liver injury.

To the mice in each Test group, the compound according to the invention (Example 4) dissolved in 4% bovine serum albumin solution was orally administered at the dose of 0.1, 1.0 and 10.0 mg/kg/day over 10 weeks in every other day.

After having lapsed 2 days from the final administration of carbon tetrachloride, a blood letting was carried out to measure GOT and GPT values in serum.

(c) Results and discussion

Results are shown in following Table 10. As apparently seen therefrom that the compound according to the invention has an action for noticeably decreasing GOT and GPT values, by the dose of 1.0 mg/kg, which were raised up by a liver injury induced by the administration of carbon tetrachloride.

TABLE 11

| Group | Dose (mg/kg) | s-GOT | s-GPT (#) (Karmen Unit) |
|---|---|---|---|
| No-treatment | — | 115 ± 9 (*) | 48 ± 6 (*) |
| Control | — | 1510 ± 112 | 1159 ± 95 |
| Test A | 0.1 | 1200 ± 180 | 1005 ± 97 |
| Test B | 1.0 | 1054 ± 140 (*) | 940 ± 83 (*) |

TABLE 11-continued

| Group | Dose (mg/kg) | s-GOT | s-GPT (#) (Karmen Unit) |
|---|---|---|---|
| Test C | 10.0 | 1020 ± 164 (*) | 1086 ± 112 |

In the Table,
\# : mean ± standard error.value, (n = 10);
\* : significant difference from Control group giving no compound ($p < 0.05$);
\*\*\* : significant difference from Control group giving no compound ($p < 0.001$).

Pharmacological Experiment 12

(Acute toxicity)

A test for determining an acute toxicity was carried out with use of ICR mice and SD rats, as experimental animals to find that each of the organogermanium compounds according to the invention show 2 g/kg or more, as the value of $LD_{50}$, so that the compounds have quite low toxicity and are excellent in safety of use.

Pharmaceutical Agent Preparation Example 1

Following ingredients are composed to prepare capsules in a conventional manner.

| Compound (Example 4) | 10 (mg) |
|---|---|
| Lactose | 165.5 |
| Hydroxypropylcellulose | 2.7 |
| Magnesium stearate | 1.8 |
| | 180 mg/capsule |

Pharmaceutical Agent Preparation Example 2

Following ingredients are composed to prepare tablets in a conventional manner.

| Compound (Example 4) | 10 (mg) |
|---|---|
| Lactose | 164.5 |
| Hydroxypropylcellulose | 2.7 |
| Light anhydrous silicic acid | 1.0 |
| Magnesium stearate | 1.8 |
| | 180 mg/tablet |

Pharmaceutical Agent Preparation Example 3

Following ingredients are composed and then freeze dried to prepare a powder for preparing an injection. The powder can be dissolved into an isonic sodium chloride solution before use.

| Compound (Example 4) | 20 (mg) |
|---|---|
| Glucose | 20 |
| Distilled water for injection | remainder |
| | 2 ml/vial |

What is claimed is:

1. An organogermanium compound of the formula

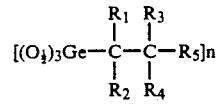 (I)

wherein $R_1$, $R_2$, $R_3$ and $R_4$ are hydrogen atom, alkyl, substituted alkyl, phenyl or substituted phenyl, and $R_5$ is a radical of

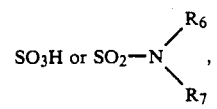

n is an integer of 2 or more, and $R_6$ and $R_7$ are hydrogen atom, alkyl, substituted alkyl, phenyl or substituted phenyl, and a salt thereof.

2. A pharmaceutical composition for use in human medicine, which comprises an effective amount of at least one organogermanium compound of the formula

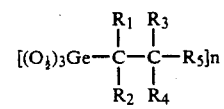 (I)

wherein $R_1$, $R_2$, $R_3$ and $R_4$ are hydrogen atom, alkyl, substituted alkyl, phenyl or substituted phenyl, and $R_5$ is a radical of

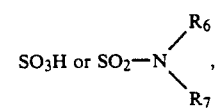

n is an integer of 2 or more, and $R_6$ and $R_7$ are hydrogen atom, alkyl, substituted alkyl, phenyl or substituted phenyl, or a salt thereof, in association with a pharmaceutically acceptable carrier or excipient.

* * * * *